United States Patent [19]

Teuerstein et al.

[11] Patent Number: 4,592,873
[45] Date of Patent: Jun. 3, 1986

[54] SULFUR-CONTAINING HALOGENATED ESTERS OF NEOPENTYL ALCOHOL AND METHODS FOR THEIR PREPARATION

[75] Inventors: Avraham Teuerstein, Omer; Rubin Scharia, Beer-Sheva; Milon Sprecher, Ramat-Gan, all of Israel

[73] Assignee: Bromine Compounds, Ltd., Beer-Sheva, Israel

[21] Appl. No.: 689,837

[22] Filed: Jan. 9, 1985

[30] Foreign Application Priority Data

Feb. 29, 1984 [IL] Israel ................................ 71108

[51] Int. Cl.⁴ ............................................. C07C 137/00
[52] U.S. Cl. ................................................... 558/59
[58] Field of Search ................................. 260/456 NS

[56] References Cited

U.S. PATENT DOCUMENTS

| | | | |
|---|---|---|---|
| 2,377,148 | 5/1945 | Heckenbleikner | 260/456 NS |
| 3,564,038 | 2/1971 | Covey et al. | 260/456 NS |
| 3,578,694 | 5/1971 | Covey et al. | 260/456 NS |

*Primary Examiner*—Nicky Chan
*Attorney, Agent, or Firm*—Frishauf, Holtz, Goodman & Woodward

[57] ABSTRACT

The present invention relates to novel compounds, useful as flame retardants for normally flammable organic polymers, which correspond to the formula:

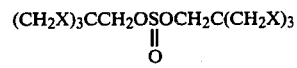

$$(CH_2X)_3CCH_2OSOCH_2C(CH_2X)_3$$
$$\underset{O}{\overset{\|}{}}$$

wherein each X is independently Br or Cl. The novel compounds may be prepared by the reaction of halogenated neopentyl alcohol with thionyl chloride.

5 Claims, No Drawings

SULFUR-CONTAINING HALOGENATED ESTERS OF NEOPENTYL ALCOHOL AND METHODS FOR THEIR PREPARATION

The present invention relates to new sulfur-containing compounds. More particularly the invention relates to new sulfur-containing halogenated neopentyl compounds.

Halogenated neopentyl alcohols are known compounds, encountered in many synthesis as starting reagents for various materials. They are easily obtained by the hydrohalogenation of pentaerythritol and are commercially available. Derivatives of halogenated neopentyl alcohol are characterized by their thermal stability which is even higher than that of the free alcohol. Derivatives of the halogenated neopentyl alcohol such as the corresponding esters are well known. Thus α,β-unsaturated carboxylic acid esters are obtained by the reaction of the tribromoneopentyl alcohol with acrylic acid in the presence of pyridine as catalyst.

It has now been discovered according to the present invention, that new compounds of sulfite esters of halogenated neopentyl alcohol having the general formula:

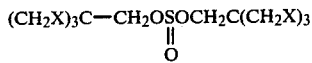

wherein each X is independently Br or Cl, are fire retardant additives for plastic materials in general and polyolefins in particular. The novel compounds according to the present invention may be any of those described by the above general formula. Especially preferred is the compound wherein each X is bromine.

Among the specific new sulfite esters of neopentyl alcohol, included in the general formula presented above, the following are mentioned:

(1) Bis(2,2-dibromomethyl-3-bromopropyl)sulfite

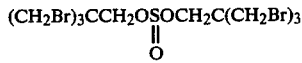

(2) Bis(2,2-dichloromethyl-3-chloropropyl)sulfite

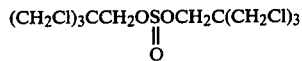

(3) Bis(2,2-dichloromethyl-3-bromopropyl)sulfite

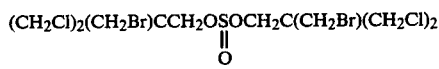

(4) Bis(2,2-dibromomethyl-3-chloropropyl)sulfite

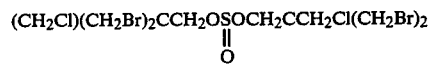

Several methods can be suggested for the preparation of the above new compounds. According to a preferred method, the new sulfite esters of the halogenated neopentyl alcohols are prepared by the reaction between the halogenated neopentyl alcohol with thionyl chloride according to the following reaction (1):

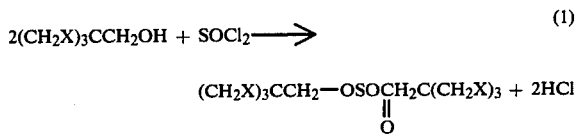

The reaction proceeds smoothly at temperature in the range of 0°–100° C. and preferably in the range of between 40°–80° C. The reaction is carried out by mixing approximately 2 moles of the neopentyl alcohol with one mole of thionyl chloride and may, if desired, be accelerated and completed by heating the mixture at a temperature of up to 100° C. or by addition of an acid scavenger much as pyridine or others as well known to those skilled is the art.

According to a most preferred embodiment, the reaction for obtaining the new sulfite ester of neopentyl alcohol, is carried out in the presence of an inert solvent e.g. aliphatic alicyclic or aromatic hydrocarbon or their halogenated compounds such as: toluene, benzene, dibromoethane, dibromomethane, chloroform, ethylene dichloride etc. The end of the reaction is indicated by the termination of the evolution of hydrogen chloride. After the reaction is completed, any residual thionyl chloride and hydrochloric acid are removed by washing or neutralization with a dilute base solution. The inert solvent is evaporated and the residue is purified by trituration with an appropriate solvent such as methanol, isopropanol etc. As the reaction occurs smoothly in absence of a solvent, the latter serves merely as diluent to decrease the speed of reaction. The amounts and nature of the solvent used, are selected according to the processability of the product as known by a person versed in the art.

According to another embodiment, the new compounds of the present invention are obtained by the reaction between oxetane and thionyl chloride according to the following reaction (2):

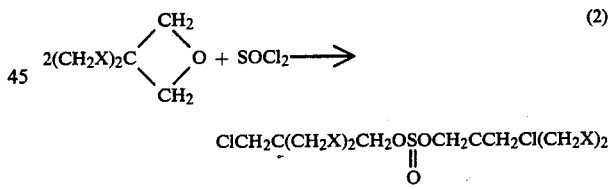

The reaction conditions are practically the same as those described above; in this case it also occurs smoothly without an inert solvent.

Another approach which might be envisaged is based on the following reaction (3):

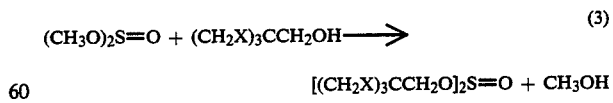

A person skilled in the art will select the appropriate method according to the availability of the reagents at site and the costs thereof.

In the following Table 1 are given some of the physical properties of the new compounds according to the present invention which are included in the general formula given on page 1.

TABLE 1

Physical properties of some of the new compounds.

| Compound No. | Molecular Weight | Elemental formula | Melting point °C. | Bromine content % | Chlorine content % |
|---|---|---|---|---|---|
| 1 | 696 | $C_{10}H_{16}Br_6O_3S$ | 69–71° C. | 68.9 | — |
| 2 | 429 | $C_{10}H_{16}Cl_6O_3S$ | 85–86° C. | — | 49.65 |
| 3 | 518 | $C_{10}H_{16}Br_2Cl_4O_3S$ | 78–79° C. | 30.8 | 27.4 |
| 4 | 607 | $C_{10}H_{16}Br_4Cl_2O_3S$ | 80–82° C. | 52.71 | 11.69 |

In order to further illustrate the nature of this invention and the manner of practising it, the following Examples are presented for clearness of understanding only and no limitation should be understood therefrom.

EXAMPLE 1

Into a glass flask provided with an agitator and condenser were introduced 162.5 g of tribromoneopentyl alcohol and 200 ml of ethylene dichloride (as solvent). Under continuous mixing at room temperature, an amount of 33 g of thionyl chloride was dropwise added to the flask. After the addition of the thionyl chloride, the flask was heated for about 4 hours at a temperature of between 70°–80° C., until the evolution of hydrogen chloride ceased. The mixture was cooled to room temperature and neutralized by a diluted ammonia solution followed by washing with water. The solvent was evaporated and the residue triturated with methanol and 140 g of pure product were obtained (i.e. 80% yield). Some physical properties of the product, compound 1) are given in Table 1.

The NMR analysis was as follows: (CDCl$_3$1 ppm) 4.24; 4.19; 4.07; 4.02 (4H, AB quarter for —CH$_2$—O— JAB=10 Hz.) P M:S (intensity) 696 (6.8); 616 (2.7); 371 (20.1); 307 (100).

EXAMPLE 2

An amount of 12 g (0.1 mole) of thionyl chloride was added dropwise to a solution of 38.3 g (0.2 mole) trichloroneopentyl alcohol in 100 cc ethylene dichloride (as inert solvent) at room temperature. At the end of the addition, the mixture was stirred and heated to reflux for four hours. Then, the mixture was cooled to room temperature, washed with water and neutralized with diluted ammonia. After the evaporation of the inert solvent and trituration of the residue with methanol, an amount of 34.7 g of white crystals was obtained as product. Some physical properties are given in Table 1 (compound 2).

EXAMPLE 3

The procedure as in Example 2 was repeated, but instead of trichloroneopentyl alcohol, an amount of 47.2 g (0.2 mole) of 2,2-dichloromethyl-3-bromo-1-propanol in 100 cc of ethylene dichloride (as inert solvent) was utilized. The product obtained, Bis(2,2-dibromomethyl-3-chloropropyl) sulfite in an amount of 43.5 g (yield 84%) in the form of white crystals, was recovered. Some physical properties are given in Table 1 (compound 4).

EXAMPLE 4

In this Example, the preparation via the oxetane is illustrated. An amount of 18 g of thionyl chloride was added to a solution of 48.8 g (0.2 mole) of dibromomethyloxetane in 100 cc of ethylene dichloride (inert solvent). The procedure was continued as in Example 2, and 44.9 g (yield 74%) of white crystals of Bis(2,2-dibromomethyl-3-chloropropyl) sulfite were recovered.

We claim:

1. A sulfite ester of halogenated neopentyl alcohol having the formula

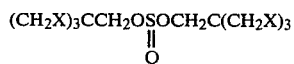

wherein each X is independently Br or Cl.

2. The sulfite ester of brominated neopentyl alcohol of claim 1 having the formula

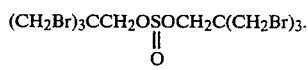

3. The sulfite ester of chlorinated neopentyl alcohol of claim 1 having the formula

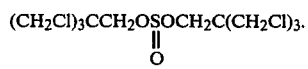

4. The sulfite ester of halogenated neopentyl alcohol of claim 1 having the formula

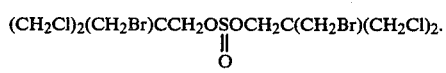

5. The sulfite ester of halogenated neopentyl alcohol of claim 1 having the formula

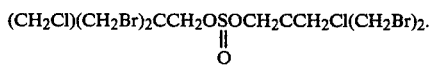

* * * * *